(12) United States Patent
Bogart

(10) Patent No.: US 7,185,524 B2
(45) Date of Patent: Mar. 6, 2007

(54) GRINDLESS SURGICAL NEEDLE MANUFACTURE

(75) Inventor: Michael W. Bogart, Milford, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 125 days.

(21) Appl. No.: 10/916,937

(22) Filed: Aug. 12, 2004

(65) Prior Publication Data
US 2005/0044922 A1   Mar. 3, 2005

Related U.S. Application Data

(60) Provisional application No. 60/494,992, filed on Aug. 14, 2003.

(51) Int. Cl.
*B21D 31/00*   (2006.01)
*B21G 3/18*   (2006.01)

(52) U.S. Cl. .................. 72/377; 72/354.2; 72/356; 72/368; 163/1; 163/5

(58) Field of Classification Search ............... 72/367.1, 72/368, 377, 341, 29.2; 606/222, 223, 224, 606/225, 226; 163/1, 5; 604/272; 430/323
See application file for complete search history.

(56) References Cited

U.S. PATENT DOCUMENTS

| 86,769 A | 2/1869 | Marriott |
|---|---|---|
| 156,795 A | 11/1874 | Jenkins |
| 221,638 A | 11/1879 | Watson |
| 292,195 A | 1/1884 | Austin |
| 324,030 A | 8/1885 | Kratz |
| 342,773 A | 6/1886 | Bailey |
| 405,536 A | 6/1889 | Curran |
| 527,263 A | 10/1894 | Blanchard |
| 722,105 A | 3/1903 | Hervey |
| 784,995 A | 3/1905 | Edwards |
| 925,953 A | 6/1909 | Sanders |
| 1,106,667 A | 8/1914 | Minahan |
| 1,110,468 A | 9/1914 | Turner |
| 1,293,660 A | 2/1919 | Armstrong |
| 1,558,037 A | 6/1925 | Morton |
| 1,599,059 A | 9/1926 | Morton |
| 2,014,170 A | 9/1935 | Everett |
| 2,092,929 A | 9/1937 | Ovington |
| 2,411,079 A | 11/1946 | Baule |
| 2,581,564 A | 1/1952 | Vittegas |
| 2,620,028 A | 12/1952 | Kohut |
| 2,811,157 A | 10/1957 | Kurtz et al. |
| 2,841,150 A | 7/1958 | Riall |
| 2,869,550 A | 1/1959 | Kurtz |
| 3,038,475 A | 6/1962 | Orcutt |

(Continued)

FOREIGN PATENT DOCUMENTS

EP   0650698 A1   5/1995

*Primary Examiner*—Dmitry Suhol

(57) ABSTRACT

A method for manufacturing a surgical needle devoid of a grinding process includes the steps of swaging a needle blank to define a substantially tapered or conical needle end, pressing the tapered needle to form a plurality of intersecting surfaces and forming cutting edges along the lines of intersection of the intersecting sides. The needle may be subjected to an etching process (e.g., an acid bath) to sharpen the cutting edges and/or provide a matte finish on the needle. The needle produced by the novel process is extremely sharp and durable, and exhibits an enhanced retention of sharpness relative to conventional ground needles over periods of prolonged use.

15 Claims, 5 Drawing Sheets

U.S. PATENT DOCUMENTS

| | | |
|---|---|---|
| 3,094,123 A | 6/1963 | Kurtz |
| 3,160,157 A | 12/1964 | Chisman |
| 3,197,997 A | 8/1965 | Kurtz |
| 3,238,942 A | 3/1966 | Lincoff |
| 3,265,070 A | 8/1966 | Kurtz |
| 3,427,764 A | 2/1969 | Draving |
| 3,545,138 A | 12/1970 | Houston |
| 3,720,021 A | 3/1973 | Wada |
| 4,128,351 A | 12/1978 | Kurtz et al. |
| 4,320,892 A | 3/1982 | Longbrake |
| 4,513,747 A | 4/1985 | Smith |
| 4,561,445 A | 12/1985 | Berke et al. |
| 4,587,202 A | 5/1986 | Borysko |
| 4,660,559 A | 4/1987 | McGregor et al. |
| 4,672,734 A | 6/1987 | Kawada et al. |
| 4,711,800 A | 12/1987 | DiVincenzo |
| 4,777,096 A | 10/1988 | Borysko |
| 4,785,868 A | 11/1988 | Koenig, Jr. |
| 4,799,483 A | 1/1989 | Kraff |
| 4,799,484 A | 1/1989 | Smith et al. |
| 4,805,292 A | 2/1989 | Noguchi |
| 4,932,961 A | 6/1990 | Wong et al. |
| 4,959,068 A | 9/1990 | Bendel et al. |
| 4,968,362 A | 11/1990 | Prasad |
| 5,002,564 A | 3/1991 | McGregor et al. |
| 5,002,565 A | 3/1991 | McGregor |
| 5,030,228 A | 7/1991 | Wong et al. |
| 5,057,401 A | 10/1991 | Borysko et al. |
| 5,100,432 A | 3/1992 | Matsutani |
| 5,103,344 A | 4/1992 | Yamamoto |
| 5,123,910 A | 6/1992 | McIntosh |
| 5,155,943 A | 10/1992 | Matsutani et al. |
| 5,178,628 A | 1/1993 | Otsuka et al. |
| 5,258,013 A | 11/1993 | Granger et al. |
| 5,263,974 A | 11/1993 | Matsutani et al. |
| 5,269,806 A | 12/1993 | Sardelis et al. |
| 5,330,441 A | 7/1994 | Prasad et al. |
| 5,342,397 A | 8/1994 | Guido |
| 5,351,518 A | 10/1994 | Bogart et al. |
| 5,380,320 A | 1/1995 | Morris |
| 5,411,613 A | 5/1995 | Rizk et al. |
| 5,464,422 A | 11/1995 | Silverman |
| 5,476,480 A | 12/1995 | Matsutani et al. |
| 5,477,604 A | 12/1995 | Smith et al. |
| 5,478,327 A | 12/1995 | McGregor et al. |
| 5,479,980 A | 1/1996 | Spingler |
| 5,526,666 A | 6/1996 | Bogart et al. |
| 5,533,982 A | 7/1996 | Rizk et al. |
| 5,539,973 A | 7/1996 | Smith et al. |
| 5,609,629 A | 3/1997 | Fearnot et al. |
| 5,626,043 A | 5/1997 | Bogart et al. |
| 5,630,268 A | 5/1997 | Smith et al. |
| 5,644,834 A | 7/1997 | Smith et al. |
| 5,649,961 A | 7/1997 | McGregor et al. |
| 5,661,893 A | 9/1997 | Smith et al. |
| 5,665,078 A | 9/1997 | McGregor et al. |
| 5,683,416 A | 11/1997 | McGregor et al. |
| 5,693,072 A | 12/1997 | McIntosh |
| 5,693,454 A | 12/1997 | Munoz |
| 5,701,656 A | 12/1997 | Smith et al. |
| 5,730,732 A | 3/1998 | Sardelis et al. |
| 5,749,897 A | 5/1998 | Matsutani et al. |
| 5,762,811 A | 6/1998 | Munoz |
| 5,776,268 A | 7/1998 | McJames et al. |
| 5,783,001 A | 7/1998 | Sardelis et al. |
| 5,792,180 A | 8/1998 | Munoz |
| 5,797,961 A | 8/1998 | Smith et al. |
| 5,814,166 A | 9/1998 | Ackerman et al. |
| 5,853,423 A | 12/1998 | McGregor et al. |
| 5,891,164 A | 4/1999 | Dabir et al. |
| 5,897,572 A | 4/1999 | Schulsinger et al. |
| 5,913,875 A | 6/1999 | Smith et al. |
| 5,928,268 A | 7/1999 | Butwell et al. |
| 6,016,682 A | 1/2000 | Tannhauser et al. |
| 6,018,860 A | 2/2000 | Smith et al. |
| 6,120,517 A | 9/2000 | Daum et al. |
| 6,214,030 B1 | 4/2001 | Matsutani et al. |
| 6,263,250 B1 | 7/2001 | Skinner |
| 6,322,581 B1 | 11/2001 | Fukuda et al. |
| 6,471,689 B1 | 10/2002 | Joseph et al. |
| 6,497,994 B1 | 12/2002 | Kafrawy |

GRINDLESS SURGICAL NEEDLE MANUFACTURE

This application claims the benefit of U.S. Provisional Application No. 60/494,992, filed Aug. 14, 2003.

BACKGROUND

1. Technical Field

The present disclosure relates to a surgical suturing needle for suturing cutaneous and subcutaneous tissue, and in particular, relates to a grindless process for manufacture of a surgical needle having enhanced penetration characteristics and retention of needle sharpness over prolonged uses.

2. Background of Related Art

Suturing needles for applying sutures, or stitches, by hand in cutaneous and sub-cutaneous tissue are well known in the art. Typically, the suturing needles are used to close wounds or adjoin adjacent tissue, often at the conclusion of a surgical procedure. Suturing needles are usually made from a cut blank of material such as stainless steel. The cut blank is metal-worked using well known machining techniques to form the suturing needle. The needle generally includes a shaft, a rear end portion with an aperture or channel to secure a suture thread and a needle head at a front end portion for puncturing skin and for passing through tissue. The needle head typically incorporates a sharpened needle tip at its distal end and cutting edges. Alternatively, the needle tip may be of a tapered configuration. Straight and curved needles including multiple curved configurations are also known in the art.

Conventional methods for needle manufacture include subjecting a needle blank to a series of grinding operations to form the desired needle edges and needle point. However, the grinding operations are often operator dependent thereby increasing the potential for needle defects. In addition, sharpened needle edges formed via conventional operations fail to retain their sharpness over extended use.

SUMMARY

Accordingly, the present disclosure is directed to a method for manufacturing a surgical needle and a surgical needle thereby produced. The preferred method is entirely devoid of a grinding process. In one preferred embodiment, the grindless process for manufacturing a surgical needle includes the steps of swaging a needle blank to define a substantially tapered or conical needle end, pressing the tapered needle to form a plurality of intersecting surfaces and forming cutting edges along the lines of intersection of the intersecting sides. The needle may be subjected to an etching process (e.g., an acid bath) to sharpen the cutting edges and/or provide a matte finish on the needle. The needle produced by the novel process is extremely sharp and durable, and exhibits an enhanced retention of sharpness relative to conventional ground needles over periods of prolonged use.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DESCRIPTION OF PREFERRED EMBODIMENTS

Figure 1:
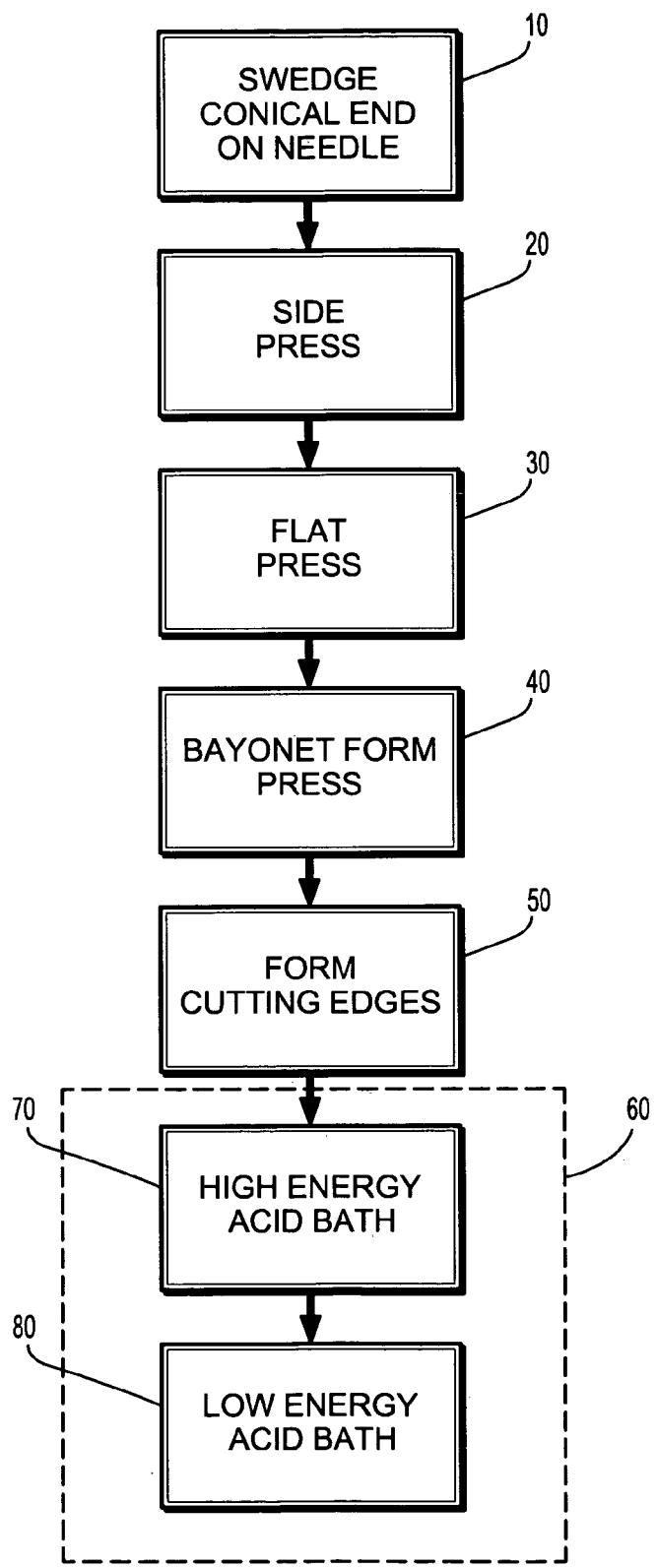
FIG. 1 is a block diagram of a preferred embodiment of a process of manufacturing a surgical needle in accordance with the principles of the present disclosure.

Preferred embodiment(s) of the process for manufacturing a surgical needle of the present disclosure will now be described in detail with reference to the drawings wherein like reference numerals identify similar or like elements throughout the several views. As used herein, the term "distal" refers to that portion which is further from the user, while the term "proximal" refers to that portion which is closest to the user.

Referring now to the block diagram of FIG. 1, there is illustrated a preferred method for needle manufacture in accordance with the principles of the present disclosure. A needle blank in the form of a cylindrical rod having a desired or predetermined length is provided. The needle blank is to be eventually formed into a surgical needle. The needle blank may be cut from suitable stock, including stainless steel, titanium or titanium alloys. The needle blank also preferably has a drilled recess in one end for receiving a surgical suture to attach the suture to the needle. It is also contemplated that the needle stock may have an open channel, an eye, etc. for receiving and attaching the suture as is known in the art.

Figure 2A:
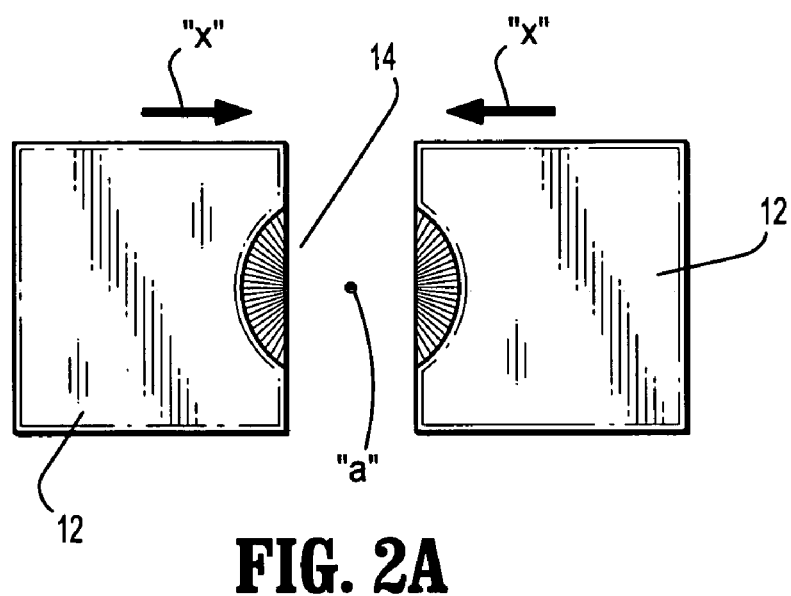
FIG. 2A is a side plan view of a pair of swaging dies utilized in the swedging operation.
Figure 2B:
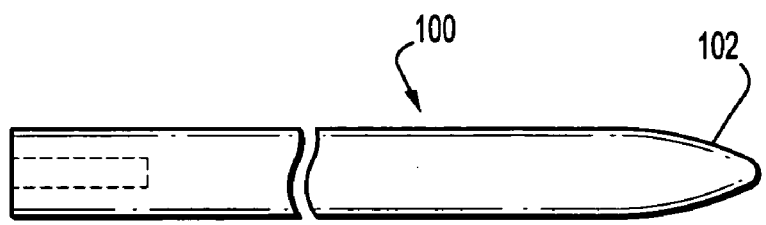
FIG. 2B is a side plan view of the needle end subsequent to the swedging operation.

With reference to FIGS. 1 and 2A, the first operation is a swaging or swedging operation 10. The needle blank is preferably placed within a collet holder of a rotary swedger apparatus. The swedger apparatus preferably includes a pair of swaging dies 12. As depicted in FIG. 2A, the dies 12 preferably have internal faces which when approximated define a conical recess 14. The dies 12 are preferably formed of a carbide material although other materials are envisioned as well. The end of the needle blank opposite the drilled end is placed within the conical recess 14 of the approximated dies. Thereafter, the swaging dies 12 are rotated about the die axis "a" to extrude a corresponding conical or tapered point on the needle end. In FIG. 2A, the dies 12 are shown in an open position. The dies 12 are movable in the direction of arrows "X" to an approximated position. FIG. 2B illustrates the configuration of the needle end of the needle blank 100 after the swedging operation. The needle end 102 is shown as generally tapered or conically shaped.

Figure 3A:
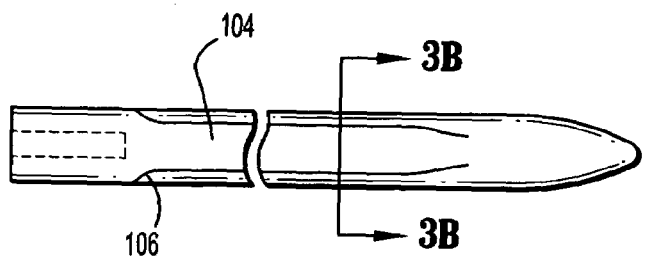
FIGS. 3A and 3B are plan and cross-sectional views of the needle subsequent to the side press operation.
Figure 3B:
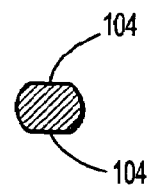

With reference again to FIG. 1, the next step in the process is a side pressing operation 20. The side pressing operation 20 is adapted to form a pair of flat surfaces on the intermediate section of the needle blank 100. The side pressing operation preferably includes a conventional press having a pair of flat dies with at least one of the dies being movable relative to the other to come together to a predetermined dimension or distance. The side pressing operation thereby defines an oval or racetrack cross-section of the intermediate section of the needle blank. The side press also results in a 3° lead in from the drilled end to the pressed intermediate section. FIGS. 3A and 3B illustrate in plan view and cross-sectional view the configuration of the needle subsequent to the side pressing operation. The flat surfaces 104 of the needle blank 100 are formed by the dies. The 3° lead-in is generally represented as reference numeral 106.

Figure 4A:
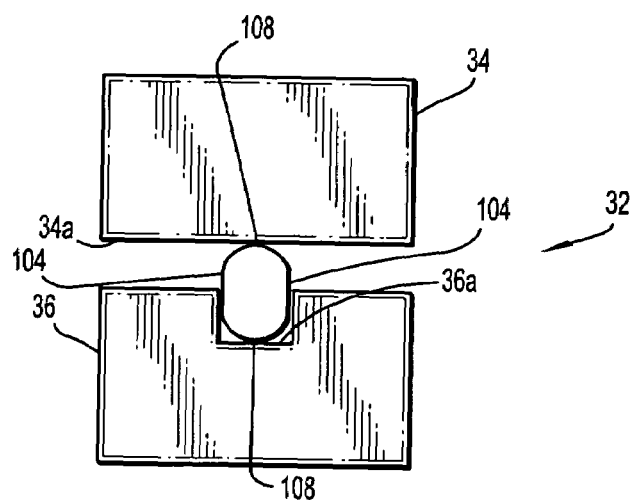
FIG. 4A is a side plan view of a pair of dies utilized in the flat press operation.
Figure 4B:
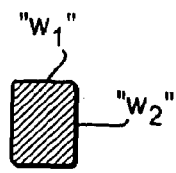
FIG. 4B is a cross-sectional view of the needle subsequent to the flat press operation.

Referring again to FIG. 1, the next step in the process is a flat press operation 30. The flat press operation 30 includes a gear-activated flat press. The press includes a box die set 32 which is best depicted in FIG. 4A. The box die is a two component die. One of the die components (e.g., the upper) 34 is movable while the second die component (e.g., the lower) 36 is stationary. The upper die 34 has a flat pressing surface 34a. The lower die 36 includes a rectangular recess 36a. The needle blank 100 is placed within the rectangular recess 36a with the flat surfaces 104 engaging the vertical walls of the rectangular recess. The press is activated. The opposing arcuate surfaces 108 of the needle 100 are then pressed whereby the needle material flows to be captured within the rectangular recess 36a. The rectangular recess 36a thereby provides a uniform collective pool for the swaged needle 100. Thus, the result of the pressing operation is the formation of a rectangular cross-section of the intermediate section of the needle. FIG. 4B illustrates a cross-section of the rectangular configuration of the needle after the flat process operation. Preferably, the cross-sectional dimension or needle width "$w_1$" across one surface of the needle (as effected by the side press) is less than the width "$w_2$" across the other surface of the needle (as effected by the flat press). Other configurations are also envisioned.

Figure 5A:
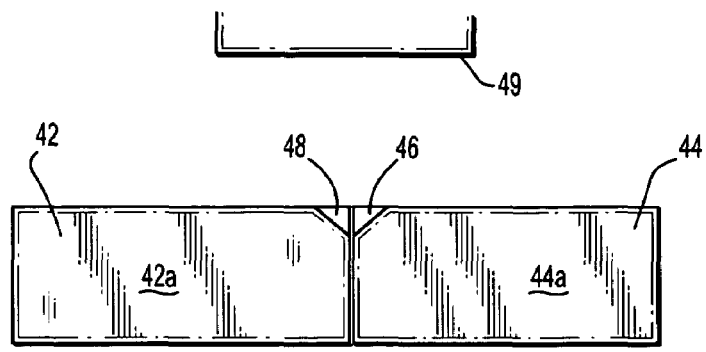
FIG. 5A is a plan view of a pair of dies utilized in the bayonet form operation.
Figure 5B:
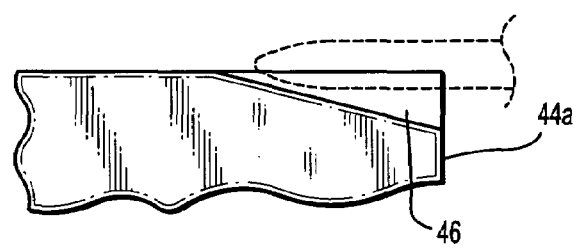
FIG. 5B is a plan view illustrating the angled cut of the dies of FIG. 5A.
Figure 5C:
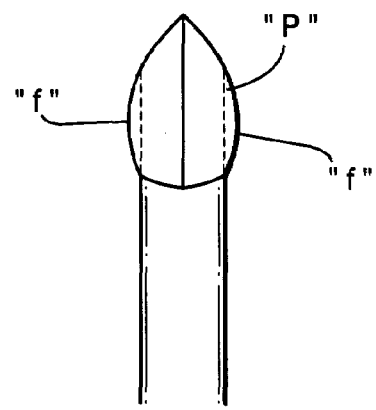
FIG. 5C is a plan view of the needle end subsequent to the bayonet form operation.

With reference again to FIG. 1, the following step in the novel process is forming a bayonet point on the needle end (STEP 40). This operation incorporates a press having two lower dies formed to define a cavity for the pressing operation. With reference to FIG. 5A, the lower dies, i.e., left and right dies 42, 44 each include an angled cut 46 in their upper surfaces which when joined together define a triangular-shaped recess 48 in cross-section tapering from the front surface 42a, 44a of the dies to the middle die area. The press further includes an upper punch 49 which moves to engage the needle. In operation, the frusto-conical needle end of the needle blank is placed within the triangular-shaped recess 48 of the left and right dies 42, 44. The press is operated such that the upper punch 49 advances to engage the needle end thereby swaging the needle end to a general bayonet or triangular shape. The process also creates an overflow flash "f" on each side of the needle of 0.002 inches to 0.003 inches in thickness thereby defining the winged appearance shown in FIG. 5C. FIG. 5C illustrates the needle end subsequent to the bayonet form process 40. The flash results from needle material overflow at a location adjacent the triangular recessed area. The flash extends radially outwardly from the normal perimeter (identified in phantom as "p") of the needle shank.

Figure 6:
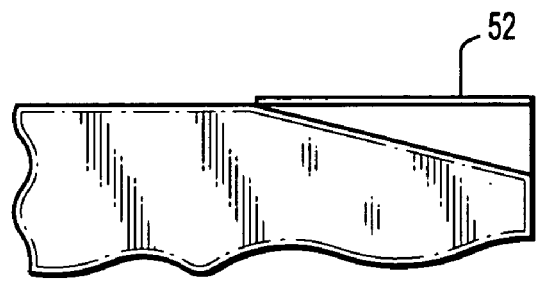
FIG. 6 is a plan view illustrating a die utilized to form the cutting edges on the needle.
Figure 7A:
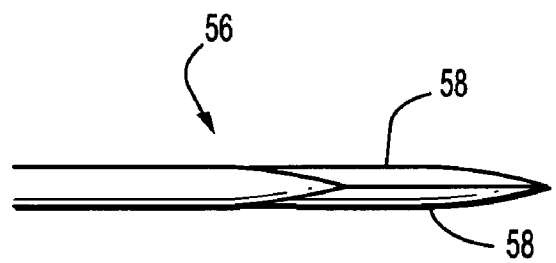
FIGS. 7A–7B are views of the needle end formed in accordance with the present disclosure.
Figure 7B:
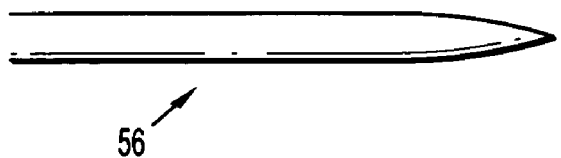

The next step in the process is to form cutting edges in the needle end by forming a crease line in the material (STEP 50). The crease line eventually serves as the peripheral cutting edges of the needle end. This operation incorporates two dies which are identical to the bayonet forming die of FIG. 5A. However, with reference to FIG. 6, the dies also incorporate a raised protrusion 52 which extends along the perimeter of the recessed areas of each die and the flat remaining surfaces of the dies. The raised protrusion 52 is preferably formed by an (electrode depositing machining EDM) process. The EDM process is coordinated to form a crease line or protrusion 52 adjacent the outer perimeter of the recess. Upon actuation of the press, the raised protrusion 52 forms a corresponding crease in the flash material adjacent location "p" (FIG. 5C) to define the bayonet configuration as shown in FIGS. 7A–7B. The crease line becomes peripheral edges which serve as cutting edges in the needle end.

FIGS. 7A–7B illustrate the bayonet needled end 56 formed in accordance with the above process. The outer cutting edges 58 are formed by way of the raised protrusions 52 of the creasing dies of FIG. 6. The central cutting edge 59 is formed along the line of intersection of the angled cuts 46 of the left and right dies 42, 44 of the bayonet form process 40. The width of the needle end "m1" (or maximum distance between cutting edges 58) is greater than the diameter of the needle stock to provide the enlarged head as shown.

The next operation is to curve the needle. This step may be formed by any conventional means. In one embodiment a curving apparatus is utilized such as the apparatus disclosed in commonly assigned U.S. Pat. No. 5,626,043 to Bogart, the contents of which are incorporated herein by reference. The curving step is optional.

The aforementioned process for needle manufacture is entirely grindless. The grindless manufacture has proven to create sharp edges along the peripheral area including the crease lines. In addition, the created edges tend to hold their sharpness over extended use relative to ground needles.

It is envisioned that the aforementioned grindless operation may be adapted to form other needle configurations besides the bayonet configuration disclosed. These alternate designs may be achieved by appropriate alternate designs to the bayonet point form press and/or the trimming/crease forming dies.

With reference again to FIG. 1, it is also contemplated that a heat treatment procedure may be employed to treat the surgical needle to enhance the surgical cutting characteristics thereof. The heat treatment procedure incorporates the step of submerging the surgical needle in an acid bath for an etching process 60. The first stage of the etching or acid bath process is a high energy step 70 where a relatively high amperage current is introduced into the bath of approximately 5–6 amps for about 20–40 seconds, preferably, 30 seconds at 12V-DC. The high energy phase aggressively moves excess flash material from the needle. The second phase in this process is a low energy step 80 and includes directing a relatively low amperage current of approximately 1 amp into the acid bath for about five minutes. This phase produces a matte-like finish on the needle. The matte finish facilitates retention of a subsequent coating which may be applied to the needle. The needle may then be coated with a suitable coating, e.g., a silicon coating, PTFE coating or Teflon.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A grindless process for manufacturing a surgical needle, comprising the steps of:
   swaging a needle blank to define a substantially tapered needle end;
   pressing the tapered needle end along a plurality of surfaces to form multiple intersecting sides on the tapered needle end; and
   engaging the tapered needle end with a die having at least one raised protrusion to form a recessed crease along an area of intersection of at least one pair of the intersection sides;
   forming at least one cutting edge adjacent the area of intersection of the at least one pair of intersecting sides.

2. The grindless process according to claim 1 wherein the step of swaging includes positioning an end of a needle blank between a pair of swaging dies defining conical recesses therein and engaging the end of the needle blank with die surfaces defining the conical recesses to form a substantially conically-shaped needle end.

3. The grindless process according to claim 2 including the step of rotating the swaging dies about the end of the needle blank.

4. The grindless process according to claim 1 further including the step of trimming excess material formed during the step of engaging.

5. The grindless process according to claim 4 wherein the step of trimming includes subjecting the tapered needle end to an acid bath.

6. The grindless process according to claim 1 wherein the step of pressing includes:
   providing a pressing die arrangement having a recess therein;
   positioning the tapered needle end at least partially within the recess; and
   punching the tapered needle end with a punch of the pressing die arrangement.

7. The grindless process according to claim 6 wherein the pressing die arrangement includes first and second angles surfaces to define a generally triangular-shaped recess whereby, during the step of punching the tapered needle end with a punch, a cutting edge is formed generally along the line of intersection of the first and second angled surfaces.

8. The grindless process according to claim 7 wherein the die includes a recess generally corresponding to the recess of the pressing die arrangement and has a pair of raised protrusions extending along opposed peripheral portions adjacent the recess, and wherein the step of engaging the tapered needle end includes the steps of:
   positioning the tapered needle end within the recess of the die; and
   punching the tapered needle end with a punch of the die whereby the pair of raised protrusions from a corresponding pair of opposed recessed creases within the tapered needle end.

9. The grindless process according to claim 8 further including the step of trimming excess material formed during the step of engaging the tapered needle end.

10. A grindless process for manufacturing a surgical needle, comprising the steps of:
    swaging a needle blank to define a substantially tapered needle end;
    pressing the tapered needle end along a plurality of surfaces to form multiple intersecting sides on the tapered needle end;
    forming cutting edges adjacent areas of intersection of the intersecting sides to define a plurality of cutting edges on the tapered needle end; and
    etching the tapered needle end to sharpen the cutting edges by subjecting the tapered needle end to an acid bath, including introducing a first current into the acid bath for a first predetermined time period and introducing a second current into the acid bath for a second predetermined time period.

11. The grindless process according to claim 10 wherein the first current ranges from about 5 amps to about 6 amps and wherein the first predetermined time period ranges from about 20 seconds to about 40 seconds.

12. The grindless process according to claim 11 wherein the second current ranges from about 0.5 amps to about 2 amps and wherein the second predetermined time period ranges from about 4 minutes to about 6 minutes.

13. A grindless process for manufacturing a surgical needle, comprising the steps of:
    forming a plurality of cutting edges along at least a portion of a needle blank; and
    subjecting at least an end portion of the needle blank to an acid bath to sharpen the cutting edges, the step of subjecting including introducing a first current into the acid bath for a first predetermined time period and introducing a second current different from the first current into the acid bath for a second predetermined time period.

14. The grindless process according to claim 13 wherein the first predetermined time period is different from the second predetermined time period.

15. The grindless process according to claim 14 wherein the first current ranges from about 5 amps to about 6 amps and wherein the first predetermined time period ranges from about 20 seconds to about 40 seconds, and wherein the second current ranges from about 0.5 amps to about 2 amps and wherein the second predetermined time period ranges from about 4 minutes to about 6 minutes.

* * * * *

UNITED STATES PATENT AND TRADEMARK OFFICE
CERTIFICATE OF CORRECTION

| | | |
|---|---|---|
| PATENT NO. | : 7,185,524 B2 | Page 1 of 1 |
| APPLICATION NO. | : 10/916937 | |
| DATED | : March 6, 2007 | |
| INVENTOR(S) | : Michael W. Bogart | |

It is certified that error appears in the above-identified patent and that said Letters Patent is hereby corrected as shown below:

Title page, item (75) Inventor: Michael W. Bogart should be --Michael W. Bogart, Milford, CT (US) and Andrew J. Vacco, Wallingford, CT (US)--

Signed and Sealed this

Nineteenth Day of June, 2007

JON W. DUDAS
*Director of the United States Patent and Trademark Office*